US008098907B2

(12) United States Patent
Yan et al.

(10) Patent No.: US 8,098,907 B2
(45) Date of Patent: Jan. 17, 2012

(54) METHOD AND SYSTEM FOR LOCAL ADAPTIVE DETECTION OF MICROANEURYSMS IN DIGITAL FUNDUS IMAGES

(75) Inventors: Xiao-Hong Michelle Yan, Princeton, NJ (US); Ke Huang, East Lansing, MI (US); Hans Schüll, Weisendorf (DE)

(73) Assignee: Siemens Corporation, Iselin, NJ (US)

( * ) Notice: Subject to any disclaimer, the term of this patent is extended or adjusted under 35 U.S.C. 154(b) by 1146 days.

(21) Appl. No.: 11/425,167

(22) Filed: Jun. 20, 2006

(65) Prior Publication Data

US 2007/0002275 A1   Jan. 4, 2007

Related U.S. Application Data

(60) Provisional application No. 60/696,242, filed on Jul. 1, 2005.

(51) Int. Cl.
*G06K 9/00* (2006.01)
*G06K 9/42* (2006.01)

(52) U.S. Cl. ........................................ 382/128; 382/257
(58) Field of Classification Search .................. 382/117, 382/115, 128–132, 254, 257, 264, 307, 308; 351/200
See application file for complete search history.

(56) References Cited

U.S. PATENT DOCUMENTS

| 5,583,659 | A  | * | 12/1996 | Lee et al. ..................... 358/3.13 |
| 5,857,030 | A  | * | 1/1999  | Gaborski et al. ............. 382/132 |
| 5,868,134 | A  | * | 2/1999  | Sugiyama et al. ............ 600/300 |
| 6,053,865 | A  | * | 4/2000  | Sugiyama et al. ............ 600/300 |
| 6,674,894 | B1 | * | 1/2004  | Parker et al. ................... 382/154 |
| 6,731,782 | B2 | * | 5/2004  | Ashton ......................... 382/131 |
| 7,474,775 | B2 | * | 1/2009  | Abramoff et al. ............. 382/128 |
| 2005/0010100 | A1 | * | 1/2005  | Hornegger et al. ........... 600/407 |
| 2005/0259854 | A1 | * | 11/2005 | Arimura et al. ............... 382/130 |
| 2006/0257031 | A1 | * | 11/2006 | Abramoff et al. ............. 382/224 |

OTHER PUBLICATIONS

Mendonça AM, Campilho AC, Nunes JR, Automatic segmentation of microaneurysms in retinal angiograms of diabetic patients. 10th International conference on Image analysis and processing. Venice, Sep. 27-29, 1999. 728-733.*
P. M. D. S. Pallawala, Wynne Hsu, Mong Li Lee, Say Song Goh, "Automated Microaneurysm Segmentation and Detection using Generalized Eigenvectors," wacv-motion, vol. 1, pp. 322-327, Seventh IEEE Workshops on Application of Computer Vision (WACV/MOTION'05)—vol. 1, 2005.*
Automatic detection of microaneurysms in color fundus images of the human retina by means of the bounding box closing. Walter, T., Klein, J.: Automatic detection of microaneurysms in color fundus images of the human retina by means of the bounding box closing. In: Proceedingsof the Third International Symposium on Medical Data Analysis. (2002) 210.*

(Continued)

*Primary Examiner* — Andrae S Allison (57) ABSTRACT

A local adaptive method is proposed for automatic detection of microaneurysms in a digital ocular fundus image. Multiple subregions of the image are automatically analyzed and adapted to local intensity variation and properties. A priori region and location information about structural features such as vessels, optic disk and hard exudates are incorporated to further improve the detection accuracy. The method effectively improves the specificity of microaneurysms detection, without sacrificing sensitivity. The method may be used in automatic level-one grading of diabetic retinopathy screening.

22 Claims, 6 Drawing Sheets

OTHER PUBLICATIONS

Andraes et al, Adaptive Document Image Thresholding Using Foreground and Background Clustering, Published in Proceedings of International Conference on Image Processing ICIP'98.*

Olson, Cree M et al., "Automated Microaneurysm Detection," Proceedings of the International Conference on Image Processing 699-702 (1996).

Kamel, M. et al., "A Neural Network Approach for the Automatic Detection of Microaneurysms in Retinal Angniograms;" Proceedings of the 2001 IEEE International Joint Conference on Neural Networks At 2694-2699 (2001).

Mendonca A.M., et al., "Automatic Segmentation of Microaneurysms in Reginal Angiograms ofo Diabetic Pataients," Proceedings of the 10th International Conference on Hnage Analysis and Processing 728-733 (2001).

Spencer, T. et al. "An image processing Strategy for the Segmentation and Quantification of Microaneurysms in Fluorescein Angiograms of the Ocular Fundus," 29 Computers and Biomedical Research at 284-302 (1996).

Ege, B. et al., "Screening tor Diabetic Retinopathy Using Computer Based Image Analysis and Statistical Classification," 62 Computer Methods and Programs in Biomedicine 165-175 (2000).

Goatman, K. "Automated detection of microaneurysms," Online Document, http://www.biomed.abdn.ac.uk/Abstracts/A07890? (1997).

Pallawale, P. et al. "Automated Microaneurysms Segmentation and Detection Using Generalized Eignevectors," Proceedings of IEEE Workshop on Application of Computer Vision (WACV) (2005).

* cited by examiner

METHOD AND SYSTEM FOR LOCAL ADAPTIVE DETECTION OF MICROANEURYSMS IN DIGITAL FUNDUS IMAGES

CROSS REFERENCE TO RELATED APPLICATIONS

This application claims the benefit of U.S. Provisional Application Ser. No. 60/696,242 entitled "A Local Adaptive Algorithm for Microaneurysms Detection in Digital Fundus Images," filed on Jul. 1, 2005, the contents of which are hereby incorporated by reference herein in their entirety.

FIELD OF THE INVENTION

The present invention relates generally to the field of medical imaging analysis, and more particularly, to techniques and systems for automatically identifying microaneurysms (MAs) in digital ocular fundus images.

BACKGROUND OF THE INVENTION

Diabetic retinopathy is a widespread eye disease that may cause blindness in diabetic patients. Often patients are not aware of the disease until its late stages, thus annual screening of patients for possible diabetic retinopathy is recommended.

In the screening, microaneurysms (MAs) are one of the earliest visible lesions in diabetic retinopathy, and are therefore an important pathology to be detected and followed closely. The number, density and locations of MAS are important factors to quantify the progression of diabetic retinopathy.

MAs are saccular outpouchings of the retinal capillaries. Their size ranges from 10 µm to 100 µm, and may be assumed always to be less 125 µm. As capillaries are too thin to be visible in a digital fundus image, MAs appear to be isolated patterns that are disconnected from the blood vessels.

Hemorrhages are blood leaking from MAs and deposited in the retina. Small dotted hemorrhages are often hard to visually differentiate from MAs. Consistent with most published work in this area, no distinction is made herein between small dotted hemorrhages and MAs.

Figure 1:
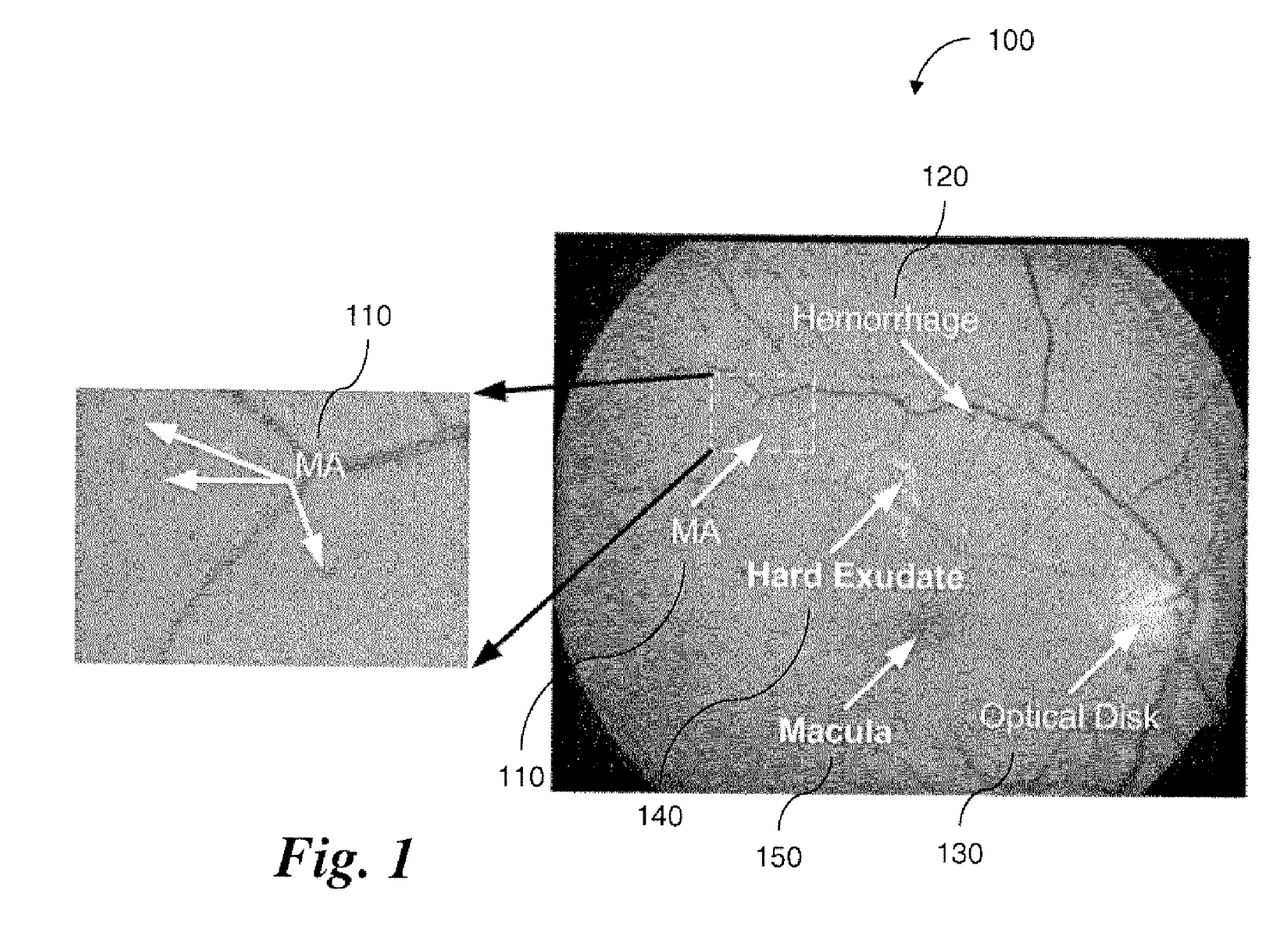
FIG. 1 is a depiction of a digital fundus image showing several structures.

FIG. 1 is an illustration of various structures contained in a digital fundus image 100. The white rectangular region in the right image is zoomed as the left image for better visibility. The ocular fundus image 100 contains several MAs 110 and a hemorrhage 120. In addition, several ocular structures appear in the image, including an optic disk 130, hard exudate 140 and the macula 150.

Manual identification of MAs in a fundus image is time-consuming and subjected to inter- and intra-operator variability. Screening a large number of diabetic patients annually poses a huge workload for ophthalmologists. A system is needed wherein MAs and other lesions are automatically and accurately detected, and only suspicious cases are referred to ophthalmologists for further evaluation and treatment.

Most existing MA detection techniques were developed for use with a fluorescein angiogram, which is an image of the ocular fundus obtained after a fluorescent dye is injected into a patient's body and passed through the blood vessels of the retina. MAs are thereby highlighted in fluorescein angiograms, making MAs detection easier.

In recent years, digital ocular fundus images, which do not require dye injection, are more commonly used in screenings. In a digital fundus image, MAs are small dark red dots several pixels in size, depending on image resolution. Although many of the techniques developed for fluorescein angiograms can be directly applied to digital fundus images, care must be taken to account for the weaker contrast of MAs to the surrounding pixels. The present invention addresses MAs detection using a digital ocular fundus image.

A number of algorithms have been proposed for MAs detection in mass screening. Most of them process digital fundus images globally without a mechanism to take into account local properties and changes in the image. Performance of those algorithms is often susceptible to non-uniform illumination and to the locations of MAs in different retinal regions. To keep sensitivity at a relatively high level, a low threshold value must be applied to the entire image globally, resulting in a much lower specificity in MAs detection. Post-processing steps, such as feature extraction and classification, must be implemented to improve the specificity at the cost of sensitivity.

Figure 2:
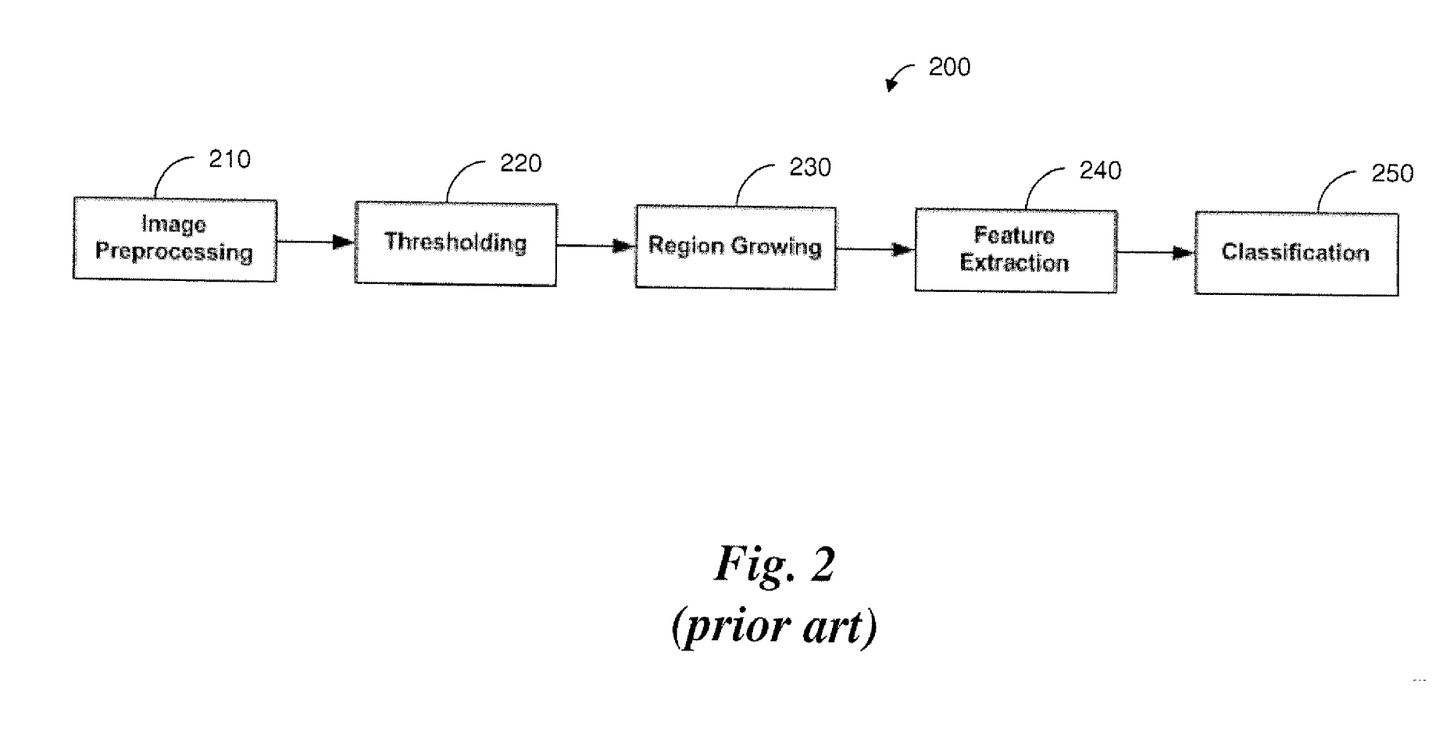
FIG. 2 is a flow chart showing a prior art method.

A widely used scheme 200 for MAs detection is shown in FIG. 2. The sequence of operations includes image preprocessing (step 210), global thresholding of the enhanced image (step 220), region growing (step 230), feature extraction (step 240) and classification (step 250) to discriminate true MAs from false detections. That technique has achieved some degree of success in MA detection; however, several factors constrain further improvement of the detection accuracy.

For example, local properties of the retina and inhomogeneous illumination of different regions are not considered in that framework. Thus, a global processing method often generates a considerable number of false detections. Some pre-processing techniques, such as shade correction, can ease the severity of inhomogeneous imaging conditions; however, the problems associated with global thresholding still exist.

The region grow, feature extraction and classification steps can remove some false detections, but those steps may also introduce additional errors. For example, region growing for small objects such as MAs is not very reliable. The shape feature in MAs detection is essential to classification; however, due to the irregular shape of MAs, the classifier is usually trained to accept shapes varying in a large range, which leads to misclassification.

Those issues exist for MAs detection using fluorescein angiograms, and are likely to be more severe with digital fundus images, where MAs appear to have much weaker contrast with neighboring pixels. In addition, all parameters in the sequential procedure 200 are coupled and affect each other; i.e., the parameters in a later processing step must be adjusted according to the output of the previous one. As a result, performance is more sensitive to parameter adjustment, and is less robust.

Another method based on normalized cuts has been proposed for MA detection. Several factors, however, may hinder its success in real applications. Its performance is sensitive to the number of segments selected, and the computational complexity can be as high as $O(n^3)$, where n is the number of pixels. The method therefore becomes impractical with digital fundus images, which are normally 1024×1280 pixels.

There is presently a need to provide a method and system for reliably detecting MAs in a digital ocular fundus image. To the inventors' knowledge, there is currently no such technique available.

SUMMARY OF THE INVENTION

In order to address the above-described problem, a local adaptive algorithm is proposed for automatic detection of MAs, where multiple subregions of each image are automatically analyzed to adapt to local intensity variations and properties. A priori structural features and pathology, such as region and location information of vessels, optic disk and hard exudates, are further incorporated to improve the detection accuracy. The method effectively improves the specificity of MA detection in digital fundus images, without sacrificing sensitivity. The technique has the potential for use in automatic level-one grading of diabetic retinopathy screening.

One embodiment of the present invention is a method for detection of microaneurysms in a digital ocular fundus image. The method comprises the steps of subdividing the image into a plurality of subregions; adaptively enhancing each subregion to correct for background variations within the subregion; and segmenting microaneurysms from a background image and from other structures in each subregion using shape features of microaneurysms and directional morphological operations.

The step of subdividing the image into a plurality of subregions may further comprise separating the regions into overlapping regions. For example, where the digital ocular fundus image is 1024×1280 pixels, the subregions may be 120 pixels per side and the regions may overlap by 10 pixels per side.

The step of image enhancing each subregion to correct for background variations within the subregion may further comprise correcting for shading effect in each subregion. The step of correcting for shading in each subregion may include the steps of estimating a background image in the subregion, and subtracting the estimated background image from an original image. The step of estimating a background image in the subregion may further include applying a low-pass two-dimensional Gaussian filter.

In addition to correcting for shading effect, the step of image enhancing each subregion may also include enhancing local contrast in the subregion, and smoothing to reduce step effects.

The step of segmenting microaneurysms from a background image and from other structures in each subregion using shape features of microaneurysms and directional morphological operations may further comprise the step of using a "Top Hat" filter to identify microaneurysms. The segmenting step may compromise the step of dilating structures in the image using a linear structuring element.

The method may further comprise the steps of identifying a structure other than a microaneurysm in the digital ocular fundus image, and discounting a false microaneurysm identification based on its location relative to the identified anatomical structures. The identified structure may be one or more of an optic disk, a hard exudate and a blood vessel.

Another embodiment of the invention is a computer program product comprising a computer readable recording medium having recorded thereon a computer program comprising code means for, when executed on a computer, instructing said computer to control steps in the method described above.

DESCRIPTION OF THE INVENTION

The inventors have developed a new scheme for robust MAs detection using digital ocular fundus images. The new scheme: (1) takes into account the local properties and variations to improve sensitivity of detection; (2) incorporates a priori knowledge during detection to further reduce false detections (such as, no MAs would appear on blood vessels); and (3) is more robust to parameter selections, and thus to different imaging conditions.

Figure 3:
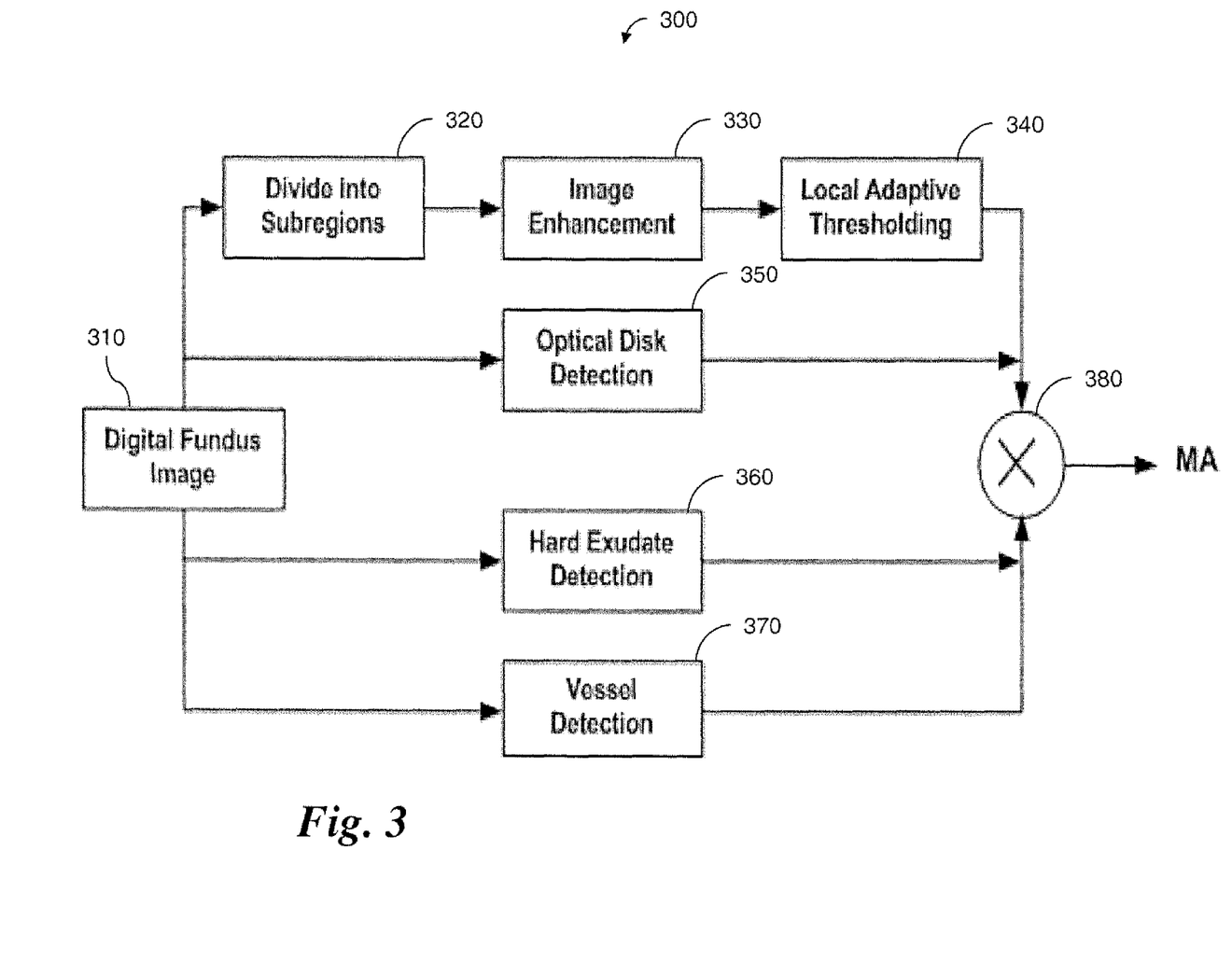
FIG. 3 is a flow chart showing a method according to one embodiment of the present invention.

A flow chart illustrating the inventive scheme 300 is shown in FIG. 3. A fundus image 310 is first automatically subdivided (step 320), and each subregion is then analyzed adaptively (steps 330, 340). Detections of optic disk (step 350), vessel regions (step 370) and hard exudates (step 360) are introduced in parallel to incorporate prior knowledge about locations where MAs would not appear. The a priori information is combined by multiplication (step 380) with the analysis results to yield accurate MAs detection.

Image Division and Enhancement

The first step in the MA detection method of the invention is to divide an entire fundus image into multiple subregions such that, in each subregion, potential MA candidates can be robustly identified. Two options are available for image division: overlapping and non-overlapping. In an overlapping scheme, neighboring subregions share common regions or pixels. In a non-overlapping scheme, no regions or pixels are shared by adjacent subregions.

Figure 4:
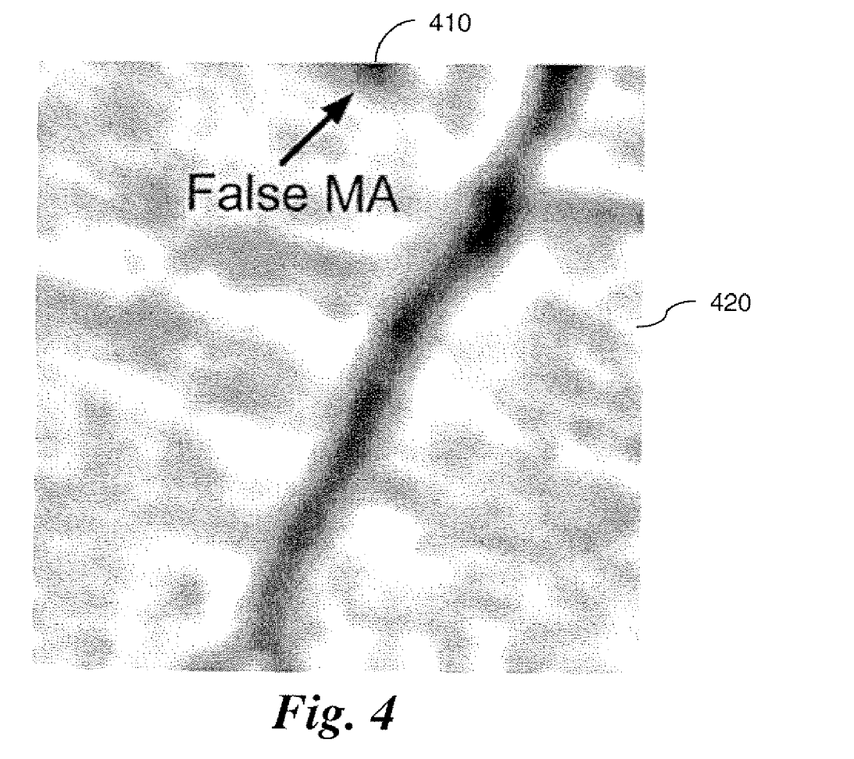
FIG. 4 is a depiction of a non-overlapping subregion of a digital fundus image.

In a preferred embodiment of the present invention, overlapping division is used to avoid generating false MA candidates. For example, a false candidate that could be generated by a non-overlapping division is shown in FIG. 4. In that example, part of another structure 410 is cropped into a subregion 420. The partial structure 410 may be mistakenly identified as an MA candidate.

In the technique of the present invention, the original fundus image is divided into subregions with a size of $M_1 \times M_2$, where only the central $m_1 \times m_2 (m_1 < M_1, m_2 < M_2)$ region is of interest. Given an image I with a size of $$N_1 \times N_2, \frac{N_1}{m_1} \times \frac{N_2}{m_2}$$

subregions are obtained, and each subregion $I_{n_1,n_2}$ is cropped from I as:

$$I_{n_1,n_2}(i, j) = I[m_1 n_1 - 0.5(M_1 - m_1) + i, m_2 n_2 - 0.5(M_2 - m_2) + j]$$

where $$0 \le i \le M_1 - 1, 0 \le j \le M_2 - 1, 0 \le n_1 \le \frac{N_1}{m_1} - 1,$$

and $$0 \leq n_2 \leq \frac{N_2}{m_2} - 1.$$

When $m_1=N_1$ and $m_2=N_2$, the local adaptive method becomes a global one. Large amounts of artifact may be generated when subregions are too small. For the typical digital fundus image size of 1024×1280, the inventors have found that $M_1=M_2=120$ and $m_1=m_2=100$ is a good compromise.

Shading effect presents slowly varying image intensity in the background, which may be due to the different physiological properties in the retina, and the nonuniform illumination across the field of view. Usually, the optic disk region is brightest in a retinal image, and macular region appears the darkest. The shading effect in MAs detection is very undesirable, and must therefore be compensated before detection. Correction for shading effect is done by first estimating a background image, and then subtracting the estimated background image from the original to correct for background variations.

In the present invention, a low-pass, 2-dimensional, 25×25 Gaussian filter may be used to estimate a background image. To enhance the visibility of small structures like MAs, contrast enhancement is applied to the difference image, with the following mapping function.

$$I = \begin{cases} a_1 t^r + b_1, & \text{if } t \leq \mu \\ a_2 t^r + b_2, & \text{if } t > \mu \end{cases}$$

where $$a_1 = 1/2 \frac{u_{max} - u_{min}}{\mu^r - t_{min}^r}, \quad b_1 = u_{min} - a_1 t_{min}^r, \quad a_2 = 1/2 \frac{u_{max} - u_{min}}{t_{max}^r - \mu^r}$$

and $$b_2 = u_{max} - a_2 t_{max}^r.$$

Figure 5:
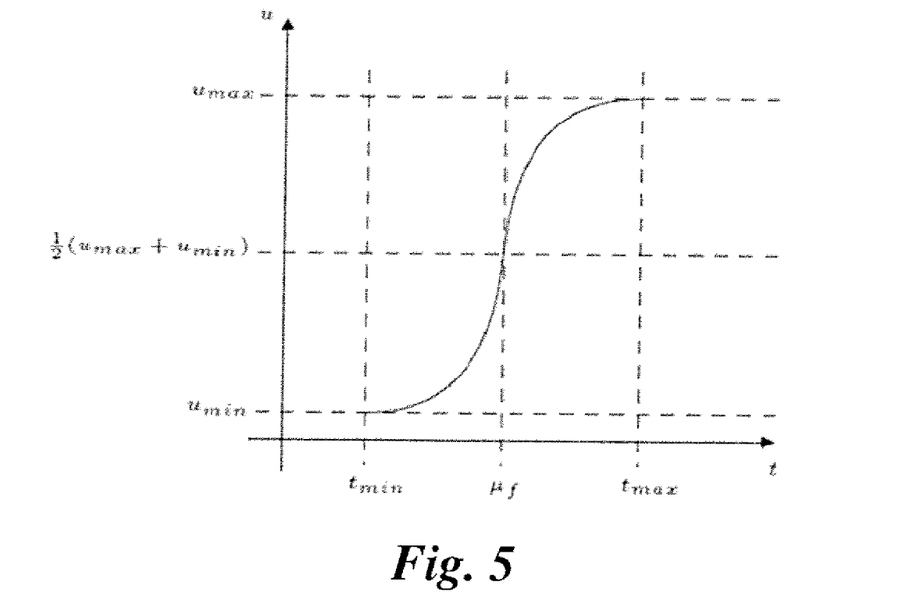
FIG. 5 is a plot showing a mapping function used for contrast enhancement in one embodiment of the present invention.

$\mu$ is the mean gray value of all pixels to be enhanced. An example of the function is shown in FIG. 5

Step effects are obvious in the difference image obtained from shading correction and contrast enhancement. To correct for step effects, a low pass filter with a small window (a 5×5 2D Gaussian filter in one example) is used to smooth the difference image.

Figure 6A:
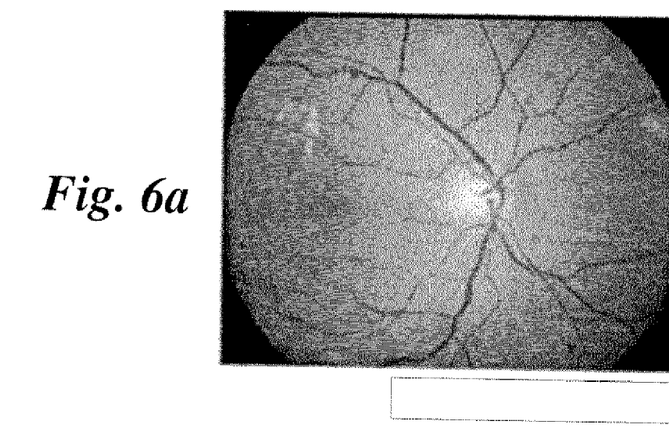
FIGS. 6a-6d are depictions of operations on a digital fundus image for shade correction and contrast enhancement according to one embodiment of the invention.
Figure 6B:
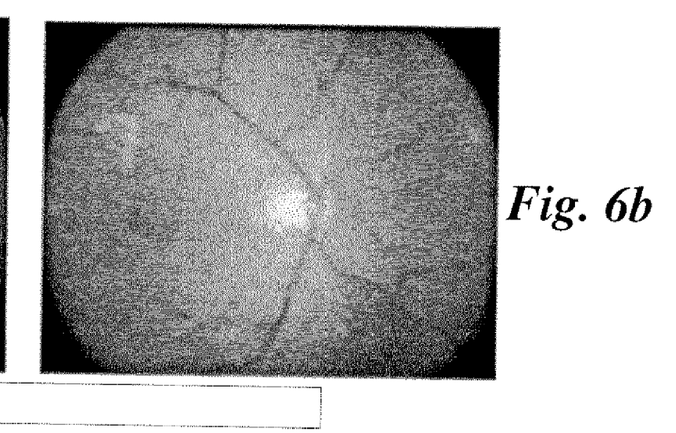
Figure 6C:
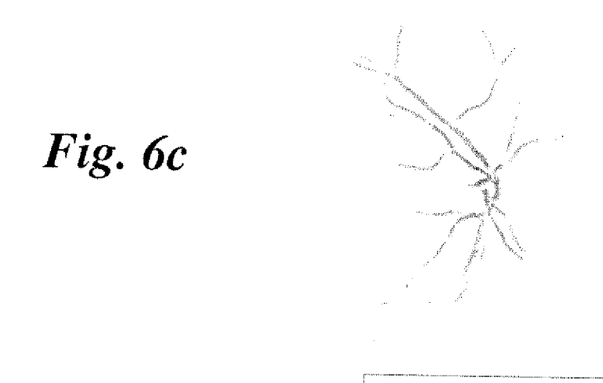
Figure 6D:
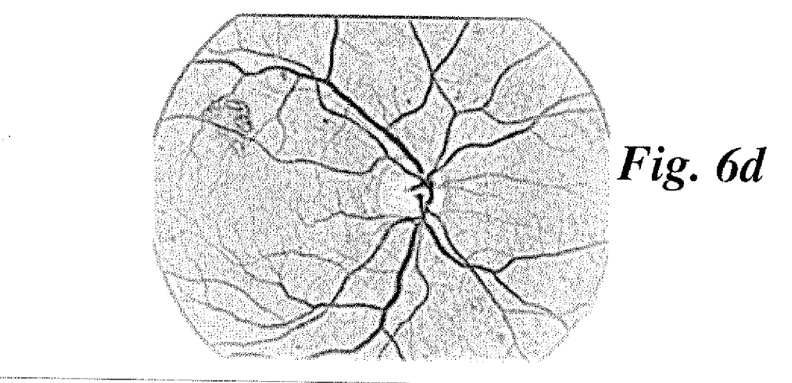

An illustration of the effect of shading correction and contrast enhancement is given in FIGS. 6a-6d. In FIG. 6a, a green channel image is shown before correction and enhancement. FIG. 6b shows an estimated background. A difference image between a green channel image and the estimated background is shown in FIG. 6c. FIG. 6d shows a difference image after contrast enhancement.

Local Adaptive MAs Detection

MAs appear to be small dark round areas in the image obtained from shading correction and contrast enhancement. Other structures, such as blood vessels and hard exudates, also appear to be dark in the same image. All valid MAs have a diameter less than 10 pixels in a 1024×1280 digital fundus image. A filter called "Top-Hat," which is based on directional morphological operations, has been developed for segmenting MAs from the background. One example of its application may be found in Cree, M., Olson, J., McHardy, K., Forrester, J., Sharp, P., *Automated Microaneurysm Detection*. Proceedings of the International Conference on Image Processing 699-702 (1996).

The operation of the "Top-Hat" filter may be described as follows. Dilation of an image I in the gray value domain is a mapping function from R to R in $R^2$ space. Given an image I and a structuring element B, the dilation operation D can be defined as:

$$D_B[I(i,j)] = \max_{(i',j') \in B(i,j)} (I(i',j'))$$

where B defines the neighboring region for (i,j). For MAs detection, a flat linear structuring element is used. Given length L and orientation angle $\theta$, the neighboring region is defined as:

$$B_L^\theta(i,j) = \{(i',j')\}, \quad i - \frac{L}{2}\sin\theta \leq i' \leq i + \frac{L}{2}\sin\theta, \quad j' = j + (i'-i)ctg\theta.$$

The "Top-Hat" filter is then defined as the minimum value obtained by rotating the structuring element at different orientation angles:

$$TH(I(i,j)) = \min_{0 < \theta < 180} \{D_{B_L^\theta}[I(i,j)]\}.$$

In the present implementation, the angle $\theta$ is incremented, and the resolution is set to an interval of 10 degrees:

$$\theta = \{10 \times n_\theta\}, 0 \leq n_\theta \leq 17$$

The length L of structuring element $B_1^\theta$ should be chosen to be larger than the diameter of a typical MA; i.e., 10. In the embodiment tested by the inventors, L is set to 15. Because MAs are isolated dark dots surrounded by relatively brighter neighboring pixels, the "Top-Hat" filter will remove MAs from the subregion, filling dark MA regions with bright pixels. For large structures like a vessel, at least in one direction, the dilation operation obtains a small value (dark pixel) from the same vessel, thus the dark pixels on the vessel are still dark after this operation.

Finally, the difference image $\delta I = TH(I) - I$ contains large values (bright pixels) for MA regions. A large value of $\delta I$ has two meanings: (1) the corresponding pixel in the original image I is from an isolated black region; and (2) the size of the black region is small (with diameter less than 15). A larger value of $\delta I$ indicates that the small black region is better contrasted.

Prior art techniques used morphological opening in the "Top-Hat" filter instead of dilation. The inventors have found that dilation gives better results for MAs detection in digital ocular fundus images.

To determine a proper threshold value for MAs detection in $\delta I$, two factors are taken into account: the area of a single MA and the absolute value of the threshold value. The pixel values of $\delta I$ are first sorted in the descending order to obtain a one-dimensional array $\delta I'$; i.e., $\delta I'(i) \geq \delta I'(j)$, given that $i \geq j$. Denoting the area of a typical MA as a, then the threshold value t is set as:

$$t = \min\{\delta I'(a), t_{low}\}$$

Note that the pixel values of $\delta I$ need not actually be sorted, because fast algorithms are well known for extracting the $a^{th}$ largest value from an unsorted array. One such algorithm is described in Cormen, T., Leiserson, C., Rivest, R., Stein, C., eds., *Introduction to Algorithms*, MIT Press (2d ed. 2001).

$t_{low}$ is placed in the formula to avoid the threshold being too high, which may occur when there are multiple MAs in a subregion. $t_{low}$ is a relatively high value, predefined to be the same for all subregions. For most subregions, $t_{low} > \delta I'(a)$. Therefore, the threshold values are automatically adapted to the properties of different image regions. For embodiments described herein, the value of a is set to 25. Each connected region in the thresholded image is taken as a candidate region $MA_n$. The mean value of $MA_n$ is calculated to reflect the confidence of the region being an MA as follows.

$$C(MA_n) = \text{mean}(\delta I(i,j)), \text{ where } (i,j) \in MA_n.$$

A higher value of $C(MA_n)$ indicates that the region is more likely a true MA, With that method, at least one MA candidate will be detected in each subregion. The MAs with low confidence values, however, will be discarded.

The enhancement procedure may introduce some artifacts: a slightly gray dot in a bright region will be enhanced to a region that has a high confidence value from δI. To address that problem, the MAs detection procedure described above is repeated on the original green channel subregion. Only regions with high confidence values from both the green channel subregion and the enhanced subregion are kept. For the original green channel subregion, $t_{low}$ is empirically set to 12, and for the enhanced subregion, $t_{low}$ is set to 100. The much higher value of $t_{low}$ for the enhanced image reflects the better contrast resulting from the enhancement step.

The technique of the present invention therefore replaces the global application of a single threshold to the entire image, with a local adaptive detection method. That technique effectively avoids generating large numbers of false detections. To illustrate, assume that an MA with confidence value $t_1$ less than $t_{low}$ exists in an image. To detect that MA, a threshold value less than $t_1$ must be applied to all regions of the image in the global thresholding method. However, in the local adaptive method, the effect of the MA with a low confidence value is confined to a single subregion.

Incorporate Prior Knowledge for MAs Detection

It is known that, physiologically, MAs do not appear in the optic disk (OD), hard exudates (HE) and blood vessel (VS). Therefore, incorporating that prior knowledge helps reduce the number of false detections. OD is the brightest region in the normal fundus image. HE appears to be yellow waxy regions with varying sizes and shapes. VS appears to be a connected tree structure distributed over the whole image. Those properties make the whole image better for detecting those structures than local subregions. Some OD/HE/VS detection algorithms are given in literature; e.g., Li, H., Chutatape, O., *A Model-Based Approach for Automated Feature Extraction in Fundus Images*, Proceedings of the International Conference on Computer Vision (2003) (Li et al.).

For OD detection, the algorithm introduced by Li et al. is simplified and applied, as follows, The gray image is first thresholded to segment the brightest pixels whose number is roughly equal to the number of pixels in a typical OD region. The segmented pixels are then clustered, and the cluster with the maximum number of pixels is selected as the original optic disk. The selected cluster is then grown to neighboring bright regions to form the final OD region.

The shape of the detected OD is not very accurate as compared to the actual OD shape. The detected GD, however, covers most of the OD region, and is good enough to remove false MAs that are likely to appear at the central OD regions when the local adaptive detection method of the invention is used.

HE has been separated in a single image using its features in a color space. Large variance in a color space, however, exists among different digital fundus images. An improved HE detection algorithm is applied by the inventors by combining both color features and texture features. The waxy structure of HE causes strong response in the "Top-Hat" filter, while other smooth yellow regions do not. That property, which exploits the texture of the HE, is utilized in the HE detection for more robust detection.

The problem of blood vessel detection has been addressed in the prior art. For the purpose of removing false MAs, the inventors utilize a computationally efficient algorithm for vessel detection based on multi-level image enhancement and binarization.

The combined result of OD/HE/VS detection is a boolean template, where "1" denotes a non-OD/HE/VS region and "0" denotes a OD/HE/VS region. As shown in FIG. 3, the multiplication (step 380) of that boolean template with the result of local adaptive MA detection generates final decisions on MAs detection.

Experiments

Experiments were conducted on twelve digital fundus images with a size of 1024×1280. Four images (labeled below from 'A1' to 'A4') are taken from healthy eyes; four images (labeled below from 'R1' to 'R4') are taken from eyes that need further treatment by ophthalmologists; the remaining four images (labeled below from 'U1' to 'U4') are taken from eyes that need immediate medical treatment. Images of type 'A' do not contain any MA, while 'R' and 'U' types of images contain different numbers of MAs.

The positions of the MAs are much more important than the number of MAs in classifying those images into the three types mentioned above. The appearance of MAs in the neighboring area of macular is enough to classify a fundus image into 'U' type, though the number of MAs may be much smaller than that of 'R' type.

Sensitivity and specificity are often used to evaluate the performance of an MA detection system. Sensitivity is defined as the probability that an MA is detected given that there is an MA in the image. Specificity is defined as the probability that no MA is detected given that the there is no MA in the image. Given an algorithm, the change in sensitivity is inversely proportional to the change in specificity.

To compare the local adaptive detection algorithm with the global detection algorithm, the inventors fixed the sensitivity to 100% (i.e., all true MAs are detected) and compared the number of false detections generated by both algorithms. In order to test the effect of incorporating prior knowledge, the number of false detections removed from the detected OD/HE/VS regions is also reported.

Results of both methods are reported in Table 1 and Table 2, separately:

TABLE I

| Global Thresholding | | | | | | | | | | | | |
|---|---|---|---|---|---|---|---|---|---|---|---|---|
| | Image | | | | | | | | | | | |
| | A1 | A2 | A3 | A4 | R1 | R2 | R3 | R4 | U1 | U2 | U3 | U4 |
| without OD/HE/VS | 25 | 23 | 10 | 16 | 68 | 56 | 60 | 43 | 20 | 15 | 62 | 72 |
| with OD/HE/VS | 14 | 12 | 4 | 9 | 45 | 42 | 41 | 32 | 13 | 8 | 27 | 23 |
| true MA | 0 | 0 | 0 | 0 | 26 | 28 | 28 | 22 | 8 | 4 | 20 | 16 |
| FP | 14 | 12 | 4 | 9 | 19 | 14 | 13 | 10 | 5 | 4 | 7 | 7 |

TABLE II

Local Adaptive Thresholding

| | \multicolumn{12}{c}{Image} |
|---|---|---|---|---|---|---|---|---|---|---|---|---|

| | A1 | A2 | A3 | A4 | R1 | R2 | R3 | R4 | U1 | U2 | U3 | U4 |
|---|---|---|---|---|---|---|---|---|---|---|---|---|
| without OD/HE/VS | 5 | 6 | 2 | 3 | 39 | 38 | 40 | 30 | 10 | 7 | 48 | 49 |
| with OD/HE/VS | 0 | 1 | 0 | 0 | 29 | 30 | 31 | 25 | 8 | 4 | 21 | 18 |
| true MA | 0 | 0 | 0 | 0 | 26 | 28 | 28 | 22 | 8 | 4 | 20 | 16 |
| FP | 0 | 1 | 0 | 0 | 3 | 2 | 3 | 3 | 0 | 0 | 1 | 2 |

In each of Table 1 and Table 2, the first row contains an index of the image, and the following four rows are: (1) the number of detected MAs without OD/HE/VS detection; (2) the number of detected MAs with OD/HE/VS detection; (3) the number of true MAs; and (4) the number of false detections with OD/HE/VS detection.

With both thresholding methods, either global or local, false MAs are more likely to be generated in the HE regions. For images 'R1' and 'R2', HE is small, and for image 'U3' and 'U4', HE is large. For those images, the effect of removing false MAs from OD/HE/VS detection is most obvious.

For all images from 'A1' to 'U4', different numbers of false MAs are removed (see the difference between the row without OD/HE/VS and the row with OD/HE/VS) by incorporating prior knowledge in both thresholding techniques. That shows that the detection of OD/HE/VS and incorporating their location information into the MAs detection is effective in removing false MAs. From those tables, it is clear that the local adaptive detection method generates fewer false detections than a global detection method. Region growing/feature extraction/statistical classifier can be applied to both global detection results and local adaptive detection results.

Figure 7A:
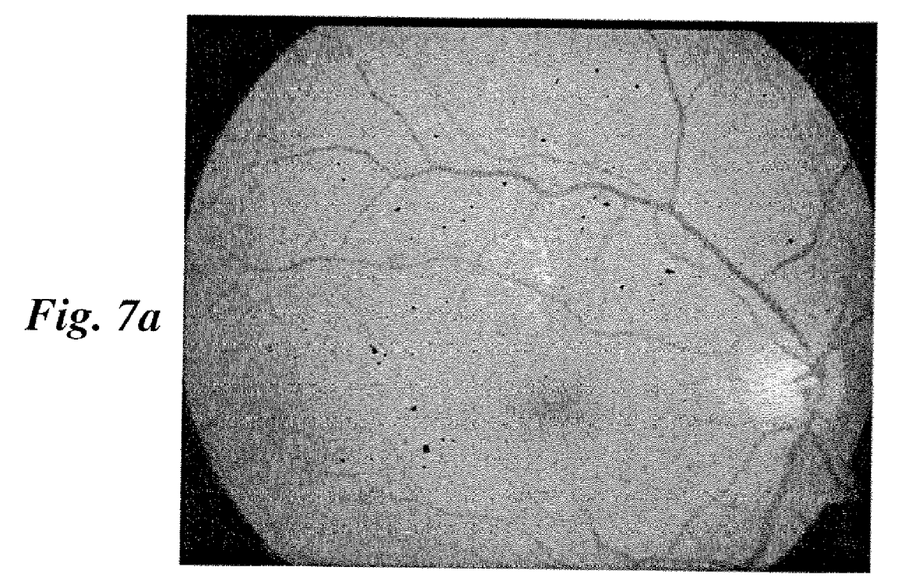
FIG. 7a is a depiction of a processed digital fundus image showing MA detection using a global method.
Figure 7B:
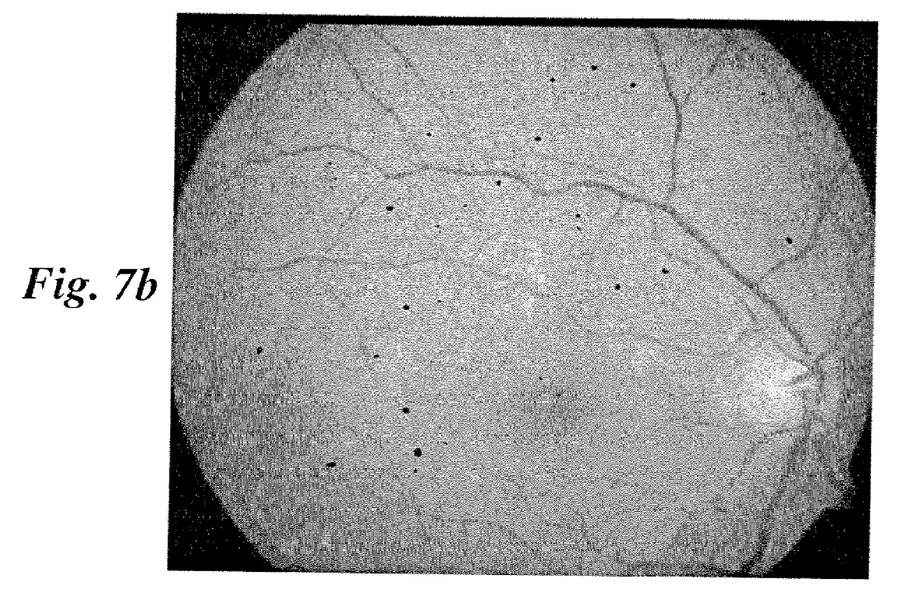
FIG. 7b is a depiction of a processed digital fundus image showing MA detection using a local adaptive method according to one embodiment of the invention.

FIG. 7 presents results from a global method (FIG. 7a) and the local adaptive method (FIG. 7b) for the same image. The detected MAs are labeled black. The results make clear that for that image, the global method generates more false detections than the local adaptive method, for the same sensitivity.

The invention is a modular framework and method and is deployed as software as an application program tangibly embodied on a program storage device. The application is accessed through a graphical user interface (GUI). The application code for execution can reside on a plurality of different types of computer readable media known to those skilled in the art. Users access the framework by accessing the GUI via a computer.

CONCLUSION

The inventors have improved two aspects of the existing MAs detection method: reducing the number of false detections through local adaptive detection and incorporating prior knowledge for MAs detection. The lower number of false MAs generated by the local adaptive detection method permits the removal of some post-processing steps, thus reducing the problem of parameter coupling and error propagation that are inherent in the sequential operations of the global detection method. Experimental results show that, compared to the existing method, the method of the invention effectively reduces the number of false detections, while keeping the detection sensitivity at a comparable level.

The foregoing Detailed Description is to be understood as being in every respect illustrative and exemplary, but not restrictive, and the scope of the invention disclosed herein is not to be determined from the Description of the Invention, but rather from the Claims as interpreted according to the full breadth permitted by the patent laws. For example, while the method is disclosed herein is applied specifically to the detection of microaneurysms in a digital ocular fundus image, the method may be applied to images made using other imaging techniques, as those techniques become available, while remaining within the scope of the invention. It is to be understood that the embodiments shown and described herein are only illustrative of the principles of the present invention and that various modifications may be implemented by those skilled in the art without departing from the scope and spirit of the invention.

What is claimed is:

1. A method for detection of candidate microaneurysms in a digital ocular fundus image, the method comprising:
    subdividing the image into a plurality of subregions;
    image enhancing each subregion to correct for background variations within the subregion, wherein each subregion is assigned a threshold value equal to a lesser of a locally adapted threshold value based on properties of the subregion and a pre-defined maximum threshold value, and the candidate microaneurysms are identified in the subregions; and
    segmenting the candidate microaneurysms from a background image and from other structures in each subregion using shape features of microaneurysms and directional morphological operations.

2. The method of claim 1, further comprising:
    separating the subregions into overlapping regions; and
    discounting a false microaneurysm by determining that a structure detected in a first overlapping region is a part of a structure other than the candidate microaneurysms detected in a second overlapping region.

3. The method of claim 2, wherein the digital ocular fundus image is 1024×1280 pixels, the subregions are 120 pixels per side and the regions overlap by 10 pixels per side.

4. The method of claim 1, wherein image enhancing each subregion to correct for background variations within the subregion, further comprises:
    correcting for shading effect in each subregion.

5. The method of claim 4, wherein correcting for shading effect in each subregion, further comprises:
    estimating a background image in the subregion; and
    subtracting the estimated background image from an original image.

6. The method of claim 5, wherein estimating a background image in the subregion, further comprises applying a low-pass two-dimensional Gaussian filter.

7. The method of claim 4, wherein image enhancing each subregion further comprises:
    enhancing contrast in the subregion; and
    smoothing to reduce step effects.

8. The method of claim 1, wherein segmenting the candidate microaneurysms from a background image and from other structures in each subregion using shape features of microaneurysms and directional morphological operations, comprises:
    using a "Top Hat" filter to identify microaneurysms.

9. The method of claim 1, wherein segmenting the candidate microaneurysms from a background image and from other structures in each subregion using shape features of microaneurysms and directional morphological operations, comprises:
    dilating structures in the image using a linear structuring element.

10. The method of claim 1, further comprising:
identifying a structure other than the candidate microaneurysms in the digital ocular fundus image; and
discounting a false microaneurysm upon detecting that a location of the false microaneurysm corresponds to a location of the identified structure other than the candidate microaneurysms.

11. The method of claim 10, wherein the identified structure other than the candidate microaneurysms is one or more of an optic disk, and a hard exudate, and identifying the hard exudate comprises combining a color feature and a texture feature of the hard exudate.

12. A computer program product comprising a non-transitory computer readable recording medium having recorded thereon a computer program comprising code means for, when executed on a computer, instructing said computer to control a method for detection of candidate microaneurysms in a digital ocular fundus image, the method comprising:
subdividing the image into a plurality of subregions;
image enhancing each subregion to correct for background variations within the subregion, wherein each subregion is assigned a threshold value equal to a lesser of a locally adapted threshold value based on properties of the subregion and a pre-defined maximum threshold value, and the candidate microaneurysms are identified in the subregions; and
segmenting the candidate microaneurysms from a background image and from other structures in each subregion using shape features of microaneurysms and directional morphological operations.

13. The computer program product of claim 12, further comprising:
separating the subregions into overlapping regions; and
discounting a false microaneurysm by determining that a structure detected in a first overlapping region is a part of a structure other than the candidate microaneurysms detected in a second overlapping region.

14. The computer program product of claim 13, wherein the digital ocular fundus image is 1024×1280 pixels, the subregions are 120 pixels per side and the regions overlap by 10 pixels per side.

15. The computer program product of claim 12, wherein image enhancing each subregion to correct for background variations within the subregion, further comprises:
correcting for shading effect in each subregion.

16. The computer program product of claim 15, wherein correcting for shading effect in each subregion, further comprises:
estimating a background image in the subregion; and
subtracting the estimated background image from an original image.

17. The computer program product of claim 16, wherein estimating a background image in the subregion, further comprises applying a low-pass two-dimensional Gaussian filter.

18. The computer program product of claim 15, wherein image enhancing each subregion further comprises:
enhancing contrast in the subregion; and
smoothing to reduce step effects.

19. The computer program product of claim 12, wherein segmenting the candidate microaneurysms from a background image and from other structures in each subregion using directional morphological operations, comprises:
using a "Top Hat" filter to locally identify microaneurysms.

20. The computer program product of claim 12, wherein segmenting the candidate microaneurysms from a background image and from other structures in each subregion using shape features of microaneurysms and directional morphological operations, comprises:
dilating structures in the image using a linear structuring element.

21. The computer program product of claim 12, wherein the method further comprises:
identifying a structure other than the candidate microaneurysms in the digital ocular fundus image; and
discounting a false microaneurysm upon detecting that a location of the false microaneurysm corresponds to a location of the identified structure other than the candidate microaneurysms.

22. The computer program product of claim 21, wherein the identified structure other than the candidate microaneurysms is one or more of an optic disk, and a hard exudate, and identifying the hard exudate comprises combining a color feature and a texture feature of the hard exudate.

* * * * *